United States Patent
Righini et al.

(10) Patent No.: US 9,056,008 B2
(45) Date of Patent: Jun. 16, 2015

(54) INSTRUMENT AND METHOD FOR IN SITU DEVELOPMENT OF CARDIAC VALVE PROSTHESES

(75) Inventors: Giovanni Righini, Chivasso (IT); Monica Achiluzzi, Chivasso (IT)

(73) Assignee: Sorin Group Italia S.r.l., Milan (IT)

(*) Notice: Subject to any disclaimer, the term of this patent is extended or adjusted under 35 U.S.C. 154(b) by 0 days.

(21) Appl. No.: 13/292,236

(22) Filed: Nov. 9, 2011

(65) Prior Publication Data

US 2012/0053684 A1 Mar. 1, 2012

Related U.S. Application Data

(63) Continuation of application No. 11/612,980, filed on Dec. 19, 2006, now Pat. No. 8,070,799.

(51) Int. Cl.
 *A61F 2/24* (2006.01)
(52) U.S. Cl.
 CPC .......... *A61F 2/2436* (2013.01); *A61F 2/2412* (2013.01); *A61F 2/243* (2013.01); *A61F 2/2433* (2013.01)
(58) Field of Classification Search
 CPC ..... A61F 2/243; A61F 2/2436; A61F 2/2433; A61F 2/2412
 See application file for complete search history.

(56) References Cited

U.S. PATENT DOCUMENTS

| | | |
|---|---|---|
| 3,514,131 A | 5/1970 | McKinney |
| 3,671,979 A | 6/1972 | Moulopoulos |
| 4,011,947 A | 3/1977 | Sawyer |
| 4,056,854 A | 11/1977 | Boretos et al. |
| 4,220,151 A | 9/1980 | Whitney |
| 4,477,930 A | 10/1984 | Totten et al. |
| 4,601,706 A | 7/1986 | Aillon |
| 4,624,822 A | 11/1986 | Arru et al. |
| 4,684,364 A | 8/1987 | Sawyer et al. |
| 4,722,725 A | 2/1988 | Sawyer et al. |
| 4,732,152 A | 3/1988 | Wallsten et al. |
| 4,758,151 A | 7/1988 | Arru et al. |
| 4,777,951 A | 10/1988 | Cribier et al. |
| 4,784,644 A | 11/1988 | Sawyer et al. |
| 4,994,077 A | 2/1991 | Dobben |
| 5,057,092 A | 10/1991 | Webster, Jr. |

(Continued)

FOREIGN PATENT DOCUMENTS

| | | |
|---|---|---|
| DE | 19546692 C2 | 6/1997 |
| DE | 29919625 U1 | 2/2000 |

(Continued)

OTHER PUBLICATIONS

European Search Report and Search Opinion of European Patent Application No. 07115960.2, dated Jan. 24, 2008.

(Continued)

*Primary Examiner* — Elizabeth Houston
*Assistant Examiner* — Son Dang
(74) *Attorney, Agent, or Firm* — Faegre Baker Daniels LLP (57) ABSTRACT

An instrument for deploying a cardiac valve prosthesis, including a plurality of radially expandable portions, at an implantation site, includes a plurality of deployment elements each independently operable to obtain the radial expansion of a radially expandable portion of the valve prosthesis. A method for deploying the cardiac valve prosthesis includes advancing the instrument to an implant site and independently actuating the radially expandable portions.

18 Claims, 7 Drawing Sheets

(56) References Cited

U.S. PATENT DOCUMENTS

| | | |
|---|---|---|
| 5,084,151 A | 1/1992 | Vallana et al. |
| 5,123,919 A | 6/1992 | Sauter et al. |
| 5,133,845 A | 7/1992 | Vallana et al. |
| 5,181,911 A | 1/1993 | Shturman |
| 5,201,757 A * | 4/1993 | Heyn et al. .................... 606/198 |
| 5,287,848 A | 2/1994 | Cubb et al. |
| 5,304,189 A | 4/1994 | Goldberg et al. |
| 5,312,393 A | 5/1994 | Mastel |
| 5,332,402 A | 7/1994 | Teitelbaum |
| 5,370,684 A | 12/1994 | Vallana et al. |
| 5,370,685 A | 12/1994 | Stevens |
| 5,387,247 A | 2/1995 | Vallana et al. |
| 5,397,351 A | 3/1995 | Pavcnik et al. |
| 5,411,552 A | 5/1995 | Andersen et al. |
| 5,423,886 A | 6/1995 | Arru et al. |
| 5,433,723 A | 7/1995 | Lindenberg et al. |
| 5,445,608 A | 8/1995 | Chen et al. |
| 5,445,646 A * | 8/1995 | Euteneuer et al. ............ 606/198 |
| 5,545,214 A | 8/1996 | Stevens |
| 5,554,185 A | 9/1996 | Block et al. |
| 5,556,414 A | 9/1996 | Turi |
| 5,662,712 A | 9/1997 | Pathak et al. |
| 5,693,083 A | 12/1997 | Baker et al. |
| 5,766,151 A | 6/1998 | Valley et al. |
| 5,772,693 A | 6/1998 | Brownlee |
| 5,782,811 A | 7/1998 | Samson et al. |
| 5,824,064 A | 10/1998 | Taheri |
| 5,840,081 A | 11/1998 | Andersen et al. |
| 5,849,005 A | 12/1998 | Garrison et al. |
| 5,855,597 A | 1/1999 | Jayaraman |
| 5,855,601 A | 1/1999 | Bessler et al. |
| 5,871,489 A | 2/1999 | Ovil |
| 5,925,063 A | 7/1999 | Khosravi |
| 5,951,600 A | 9/1999 | Lemelson |
| 5,954,766 A | 9/1999 | Zadno Azizi et al. |
| 5,957,949 A | 9/1999 | Leonhardt et al. |
| 5,968,068 A | 10/1999 | Dehdashtian et al. |
| 5,980,570 A | 11/1999 | Simpson |
| 6,010,530 A | 1/2000 | Goicoechea |
| 6,010,531 A | 1/2000 | Donlon et al. |
| 6,019,756 A | 2/2000 | Mueller et al. |
| 6,019,790 A | 2/2000 | Holmberg et al. |
| 6,029,671 A | 2/2000 | Stevens et al. |
| 6,030,360 A | 2/2000 | Biggs |
| 6,090,099 A | 7/2000 | Samson et al. |
| 6,106,497 A | 8/2000 | Wang |
| 6,125,852 A | 10/2000 | Stevens et al. |
| 6,139,572 A | 10/2000 | Campbell et al. |
| 6,168,614 B1 | 1/2001 | Andersen et al. |
| 6,174,307 B1 | 1/2001 | Daniel et al. |
| 6,251,093 B1 | 6/2001 | Valley et al. |
| 6,299,638 B1 | 10/2001 | Sauter |
| 6,309,382 B1 | 10/2001 | Garrison et al. |
| 6,346,071 B1 | 2/2002 | Mussivand |
| 6,395,017 B1 | 5/2002 | Dwyer et al. |
| 6,402,780 B2 | 6/2002 | Williamson, IV et al. |
| 6,416,474 B1 | 7/2002 | Penner et al. |
| 6,425,916 B1 * | 7/2002 | Garrison et al. ............ 623/2.11 |
| 6,454,799 B1 | 9/2002 | Schreck |
| 6,458,153 B1 | 10/2002 | Bailey et al. |
| 6,482,228 B1 | 11/2002 | Norred |
| 6,572,642 B2 | 6/2003 | Rinaldi et al. |
| 6,582,462 B1 | 6/2003 | Andersen et al. |
| 6,607,553 B1 | 8/2003 | Healy et al. |
| 6,641,558 B1 | 11/2003 | Aboul Hosn et al. |
| 6,645,197 B2 | 11/2003 | Garrison et al. |
| 6,645,220 B1 | 11/2003 | Huter et al. |
| 6,652,578 B2 | 11/2003 | Bailey et al. |
| 6,685,739 B2 | 2/2004 | DiMatteo et al. |
| 6,726,648 B2 | 4/2004 | Kaplon et al. |
| 6,726,651 B1 | 4/2004 | Robinson et al. |
| 6,726,712 B1 | 4/2004 | Raeder Devens et al. |
| 6,730,118 B2 | 5/2004 | Spenser et al. |
| 6,733,525 B2 | 5/2004 | Yang et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,830,584 B1 | 12/2004 | Seguin |
| 6,830,585 B1 | 12/2004 | Artof et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,913,618 B2 | 7/2005 | Denardo et al. |
| 6,945,957 B2 | 9/2005 | Freyman |
| 6,964,673 B2 | 11/2005 | Tsugita et al. |
| 6,974,464 B2 | 12/2005 | Quijano et al. |
| 6,981,942 B2 | 1/2006 | Khaw et al. |
| 6,991,646 B2 | 1/2006 | Clerc et al. |
| 7,001,423 B2 | 2/2006 | Euteneuer et al. |
| 7,018,406 B2 | 3/2006 | Seguin et al. |
| 7,018,408 B2 | 3/2006 | Bailey et al. |
| 7,041,132 B2 | 5/2006 | Quijano et al. |
| 7,044,966 B2 | 5/2006 | Svanidze et al. |
| 7,077,801 B2 | 7/2006 | Haverich |
| 7,101,396 B2 | 9/2006 | Artof et al. |
| 7,144,364 B2 | 12/2006 | Barbut et al. |
| 7,156,872 B2 | 1/2007 | Strecker |
| 7,195,641 B2 | 3/2007 | Palmaz et al. |
| 7,201,761 B2 | 4/2007 | Woolfson et al. |
| 7,329,279 B2 | 2/2008 | Haug et al. |
| 7,338,467 B2 | 3/2008 | Lutter |
| 7,338,520 B2 | 3/2008 | Bailey et al. |
| 7,374,571 B2 | 5/2008 | Pease et al. |
| RE40,377 E | 6/2008 | Williamson, IV et al. |
| 7,399,315 B2 | 7/2008 | Iobbi |
| 7,544,206 B2 | 6/2009 | Cohn |
| 7,556,646 B2 | 7/2009 | Yang et al. |
| 7,591,843 B1 | 9/2009 | Escano et al. |
| 7,618,432 B2 | 11/2009 | Pedersen et al. |
| 7,635,386 B1 | 12/2009 | Gammie |
| 7,708,775 B2 | 5/2010 | Rowe et al. |
| 7,896,915 B2 | 3/2011 | Guyenot et al. |
| 7,993,392 B2 | 8/2011 | Rihhini et al. |
| 8,057,539 B2 | 11/2011 | Ghione et al. |
| 8,070,799 B2 | 12/2011 | Righini et al. |
| 8,114,154 B2 | 2/2012 | Righini et al. |
| 8,470,024 B2 | 6/2013 | Ghione et al. |
| 8,475,521 B2 | 7/2013 | Suri et al. |
| 8,486,137 B2 | 7/2013 | Suri et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0039450 A1 | 11/2001 | Pavcnik et al. |
| 2001/0044591 A1 | 11/2001 | Stevens et al. |
| 2002/0029075 A1 | 3/2002 | Leonhardt |
| 2002/0042651 A1 | 4/2002 | Liddicoat et al. |
| 2002/0045846 A1 | 4/2002 | Kaplon et al. |
| 2002/0045929 A1 | 4/2002 | Diaz |
| 2002/0058995 A1 | 5/2002 | Stevens |
| 2002/0099431 A1 | 7/2002 | Armstrong et al. |
| 2002/0107531 A1 | 8/2002 | Schreck et al. |
| 2002/0117264 A1 | 8/2002 | Rinaldi et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0033000 A1 | 2/2003 | DiCaprio et al. |
| 2003/0036795 A1 | 2/2003 | Andersen et al. |
| 2003/0055495 A1 | 3/2003 | Pease et al. |
| 2003/0109924 A1 | 6/2003 | Cribier |
| 2003/0130729 A1 | 7/2003 | Paniagua et al. |
| 2003/0153974 A1 | 8/2003 | Spenser et al. |
| 2003/0163194 A1 | 8/2003 | Quijano et al. |
| 2003/0191521 A1 | 10/2003 | Denardo et al. |
| 2003/0191528 A1 | 10/2003 | Quijano et al. |
| 2004/0034411 A1 | 2/2004 | Quijano et al. |
| 2004/0039371 A1 | 2/2004 | Tockman et al. |
| 2004/0039436 A1 | 2/2004 | Spenser et al. |
| 2004/0039442 A1 | 2/2004 | St. Goar et al. |
| 2004/0049266 A1 | 3/2004 | Anduiza et al. |
| 2004/0055606 A1 | 3/2004 | Hendricksen et al. |

(56) References Cited

U.S. PATENT DOCUMENTS

| | | |
|---|---|---|
| 2004/0078072 A1 | 4/2004 | Tu et al. |
| 2004/0093060 A1 | 5/2004 | Seguin et al. |
| 2004/0093063 A1 | 5/2004 | Wright et al. |
| 2004/0106976 A1 | 6/2004 | Bailey et al. |
| 2004/0127848 A1 | 7/2004 | Freyman |
| 2004/0147993 A1 | 7/2004 | Westlund et al. |
| 2004/0186563 A1 | 9/2004 | Lobbi |
| 2004/0215333 A1 | 10/2004 | Duran et al. |
| 2004/0236170 A1 | 11/2004 | Kim |
| 2004/0249413 A1 | 12/2004 | Allen et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0096993 A1 | 5/2005 | Pradhan et al. |
| 2005/0104957 A1 | 5/2005 | Okamoto et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bergheim |
| 2005/0251251 A1 | 11/2005 | Cribier |
| 2005/0267493 A1 | 12/2005 | Schreck et al. |
| 2005/0278010 A1 | 12/2005 | Richardson |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0064054 A1 | 3/2006 | Sakakine et al. |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen et al. |
| 2006/0271081 A1 | 11/2006 | Realyvasquez |
| 2006/0276775 A1 | 12/2006 | Rosenberg et al. |
| 2007/0005131 A1 | 1/2007 | Taylor |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0156225 A1 | 7/2007 | George et al. |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Strommer et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1 | 8/2008 | Cerier |
| 2008/0262507 A1 | 10/2008 | Righini et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1 | 7/2010 | Alkhatib |
| 2010/0292782 A1 | 11/2010 | Giannetti et al. |
| 2010/0292783 A1 | 11/2010 | Giannetti et al. |
| 2010/0292784 A1 | 11/2010 | Giannetti et al. |
| 2013/0123915 A1 | 5/2013 | Giannetti et al. |

FOREIGN PATENT DOCUMENTS

| | | |
|---|---|---|
| DE | 19857887 A1 | 5/2005 |
| EP | 0133420 B1 | 2/1988 |
| EP | 0155245 B1 | 5/1990 |
| EP | 0637454 B1 | 2/1995 |
| EP | 0592410 B1 | 10/1995 |
| EP | 0512359 B1 | 12/1996 |
| EP | 0515324 B1 | 12/1996 |
| EP | 0850607 A1 | 7/1998 |
| EP | 0941716 B1 | 9/1999 |
| EP | 1057460 A1 | 12/2000 |
| EP | 1059271 A1 | 12/2000 |
| EP | 1356763 A2 | 10/2003 |
| EP | 1356793 A2 | 10/2003 |
| EP | 0852481 B1 | 2/2004 |
| EP | 1440671 A2 | 7/2004 |
| EP | 1088529 B1 | 6/2005 |
| EP | 0955895 B1 | 8/2005 |

(56) References Cited

FOREIGN PATENT DOCUMENTS

| | | |
|---|---|---|
| EP | 1488735 B1 | 6/2007 |
| EP | 1212989 B1 | 1/2008 |
| EP | 1653884 B1 | 6/2008 |
| EP | 1935377 A1 | 6/2008 |
| EP | 1955643 A1 | 8/2008 |
| EP | 1978895 B1 | 10/2008 |
| EP | 1986579 B1 | 11/2008 |
| EP | 1570809 B1 | 1/2009 |
| EP | 2033581 A1 | 3/2009 |
| EP | 2033597 A1 | 3/2009 |
| FR | 2828091 A1 | 2/2003 |
| WO | WO9511055 A1 | 4/1995 |
| WO | WO9724989 A1 | 7/1997 |
| WO | WO9817202 A1 | 4/1998 |
| WO | WO9829057 A1 | 7/1998 |
| WO | WO9853761 A1 | 12/1998 |
| WO | WO9904728 A1 | 2/1999 |
| WO | WO9912483 A1 | 3/1999 |
| WO | WO9956665 A1 | 11/1999 |
| WO | WO0018303 A1 | 4/2000 |
| WO | WO0041525 A2 | 7/2000 |
| WO | WO0041652 A1 | 7/2000 |
| WO | WO0121244 A1 | 3/2001 |
| WO | WO0162189 A1 | 8/2001 |
| WO | WO0164137 A1 | 9/2001 |
| WO | WO0176510 A2 | 10/2001 |
| WO | WO02041789 A2 | 8/2002 |
| WO | WO02076348 A1 | 10/2002 |
| WO | WO02047575 A2 | 12/2002 |
| WO | WO03047468 A1 | 6/2003 |
| WO | WO03003943 A2 | 11/2003 |
| WO | WO03094797 A1 | 11/2003 |
| WO | WO2004019825 A1 | 3/2004 |
| WO | WO2004028399 A2 | 4/2004 |
| WO | WO2004089253 A1 | 10/2004 |
| WO | WO2005046525 A1 | 5/2005 |
| WO | WO2005065200 A2 | 7/2005 |
| WO | WO2005096993 A1 | 10/2005 |
| WO | WO2005104957 A2 | 11/2005 |
| WO | WO2006009690 A1 | 1/2006 |
| WO | WO2006014233 A2 | 2/2006 |
| WO | WO2006054107 A2 | 5/2006 |
| WO | WO2006063199 A2 | 6/2006 |
| WO | WO2006076890 A1 | 7/2006 |
| WO | WO2006086135 A2 | 8/2006 |
| WO | WO2006089517 A1 | 8/2006 |
| WO | WO2006116558 A2 | 11/2006 |
| WO | WO2006135551 A2 | 12/2006 |
| WO | WO2006138173 A2 | 12/2006 |
| WO | WO2007021708 A1 | 2/2007 |
| WO | WO2007033093 A2 | 3/2007 |
| WO | WO2007059252 A1 | 5/2007 |
| WO | WO2007071436 A2 | 6/2007 |
| WO | WO2007076463 A2 | 7/2007 |
| WO | WO2008031103 A2 | 3/2008 |
| WO | WO2008097589 A1 | 8/2008 |
| WO | WO2008125153 A1 | 10/2008 |
| WO | WO2008138584 A1 | 11/2008 |

OTHER PUBLICATIONS

European Search Report Issued in EP 09160184 dated Oct. 22, 2009.
European Search Report issued in EP 11182402, mailed Nov. 16, 2011, 5 pages.
European Search Report issued in EP Application 08163752, dated Dec. 29, 2008.
European Search Report Issued in EP Application No. 07115951, dated Sep. 24, 2009, 8 pages.
European Search Report issued in EP Application No. 08159301, mailed Dec. 30, 2008, 6 pages.
European Search Report Issued in EP Application No. 09160183, dated Sep. 29, 2009, 6 pages.
European Search Report Issued in EP Application No. 09160186, dated Oct. 6, 2009, 5 pages.
Extended European Search Report issued in EP Application 06126552, dated Jun. 6, 2007, 7 pages.
Extended European Search Report issued in EP Application 06126556, dated Jul. 6, 2007, 13 pages.
Extended European Search Report issued in EP Application 07115960, dated Jan. 24, 2008, 8 pages.
Extended European Search Report issued in EP Application 09158822, dated Sep. 29, 2009, 5 pages.
Ho, Paul C., "Percutaneous aortic valve replacement: A novel design of the delivery and deployment system", Minimally Invasive Therapy, 2008; 17:3; 190-194.
Huber et al., "Direct-Access Valve Replacement: A Novel Approach for Off-Pump Valve Implantation Using Valved Stents", Journal for the American College of Cardiology, pp. 366-370, vol. 46, No. 2, Jul. 19, 2005, ISSN: 0735-1097/05, published on-line Jul. 5, 2005.
Partial European Search Report issued in EP App No. 06126556, mailed Apr. 16, 2007, 6 pages.
Partial European Search Report issued in EP Application No. 10155332, dated Jun. 9, 2011, 7 pages.
U.S. Appl. No. 11/851,528, filed Sep. 7, 2007.

* cited by examiner

INSTRUMENT AND METHOD FOR IN SITU DEVELOPMENT OF CARDIAC VALVE PROSTHESES

CROSS-REFERENCE TO RELATED APPLICATION

This application is a continuation of U.S. patent application Ser. No. 11/612,980, entitled "Instrument and Method for In Situ Deployment of Cardiac Valve Prostheses," filed Dec. 19, 2006, now U.S. Pat. No. 8,070,799, which is herein incorporated by reference in its entirety.

This application is related to U.S. patent application Ser. No. 11/612,972, entitled "Device for In Situ Axial and Radial Positioning of Cardiac Valve Prostheses," U.S. patent application Ser. No. 11/612,974, entitled "System for In Situ Positioning of Cardiac Valve Prostheses without Occluding Blood Flow," now U.S. Pat. No. 8,057,539, and U.S. patent application Ser. No. 11/612,968, entitled "Device for In Situ Positioning of Cardiac Valve Prostheses," all of which were filed on even date herewith and are hereby incorporated by reference.

TECHNICAL FIELD

The present invention relates to instruments for the in situ delivery and positioning of implantable devices. In particular, the invention relates to the in situ delivery of expandable prosthetic cardiac valves.

BACKGROUND

Recently, there has been increasing consideration given to the possibility of using, as an alternative to traditional cardiac-valve prostheses, valves designed to be implanted using minimally-invasive surgical techniques or endovascular delivery (so-called "percutaneous valves"). Implantation of a percutaneous valve (or implantation using thoracic-microsurgery techniques) is a far less invasive act than the surgical operation required for implanting traditional cardiac-valve prostheses.

These expandable prosthetic valves typically include an anchoring structure or armature, which is able to support and fix the valve prosthesis in the implantation position, and prosthetic valve elements, generally in the form of leaflets or flaps, which are stably connected to the anchoring structure and are able to regulate blood flow. One exemplary expandable prosthetic valve is disclosed in U.S. Publication 2006/0178740 A1, which is incorporated herein by reference in its entirety.

An advantage of these expandable prosthetic valves is that they enable implantation using various minimally invasive or sutureless techniques. One non-limiting exemplary application for such an expandable valve prosthesis is for aortic valve replacement. Various techniques are generally known for implanting such an aortic valve prosthesis and include percutaneous implantation (e.g., transvascular delivery through a catheter), dissection of the ascending aorta using minimally invasive thoracic access (e.g., mini-thoracotomy), and transapical delivery wherein the aortic valve annulus is accessed directly through an opening near the apex of the left ventricle. Note that the percutaneous and thoracic access approaches involve delivering the prosthesis in a direction opposing blood flow (i.e., retrograde), whereas the transapical approach involves delivering the prosthesis in the same direction as blood flow (i.e., antegrade) Similar techniques may also be applied to implant such a cardiac valve prosthesis at other locations (e.g., a pulmonary valve annulus).

Further problems in the art include positioning the prosthetic valve in the right location as well as centering the valve prior to implantation.

There is a need in the art for delivery and implantation instruments capable of delivering an expandable prosthetic valve to a precise location associated with a corresponding valve annulus. There is a further need for instruments adapted to carefully control expansion of the valve to prevent the valve from misaligning during valve expansion. Finally, there is a need for an instrument adapted to remove such a prosthetic valve.

SUMMARY

The present invention, according to one embodiment, is a cardiac valve implantation system for implanting a cardiac valve prosthesis at an implantation site associated with a cardiac valve annulus. The system includes an expandable cardiac valve prosthesis including a plurality of radially expandable portions and a plurality of valve leaflets. It further includes a deployment instrument including a control handle and a plurality of independently operable deployment elements operable to deploy the plurality of radially expandable portions. The system also includes a delivery device adapted to provide a pathway from outside the patient's body for delivery of the deployment instrument to the implantation site.

The present invention, according to another embodiment, is a minimally-invasive method of implanting an expandable cardiac valve prosthesis including an annular inflow portion and an annular outflow portion at an implantation site. The method includes positioning the cardiac valve prosthesis in a deployment instrument including first and second independently operable deployment elements associated with the annular inflow portion and the annular outflow portion respectively, advancing the deployment instrument to the implantation site, actuating one of the first and second elements to cause the corresponding annular portion of the prosthesis to expand and engage the implantation site, and actuating the other of the first and second elements to cause the other corresponding annular portion of the prosthesis to expand and engage the implantation site.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 3a-3e illustrate a sequence of deploying a prosthetic heart valve using a retrograde approach, according to one embodiment of the present invention.

FIGS. 4a-4e illustrate a sequence of deploying a prosthetic heart valve using an antegrade approach, according to another embodiment of the present invention.

FIGS. 5a-5c illustrate a sequence of deploying a prosthetic heart valve, according to yet another embodiment of the present invention.

FIG. 10a-10d illustrate a sequence of deploying a prosthetic heart valve, according to another embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1A:
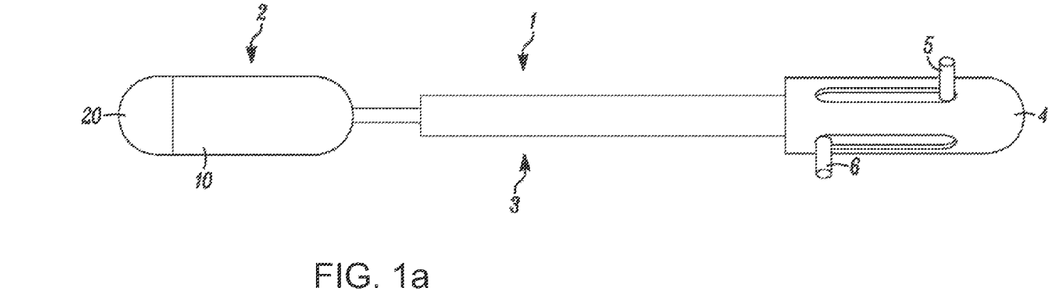
FIGS. 1a and 1b illustrate, in general terms, the delivery instrument of the present invention, according to two exemplary embodiments.
Figure 1B:
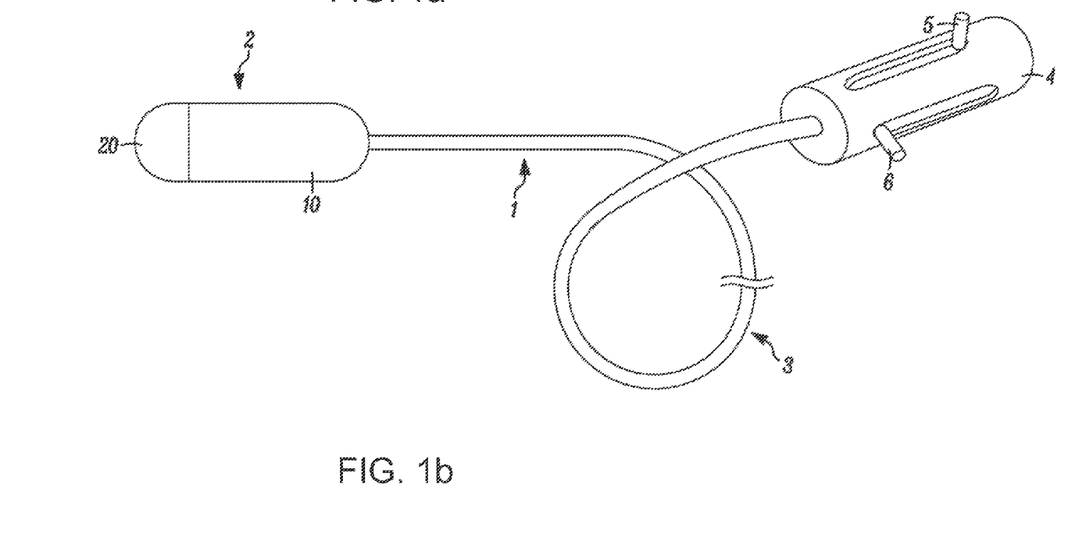

FIGS. 1a and 1b show an instrument 1 for implanting and radially deploying in situ an expandable, prosthetic cardiac valve. Purely by way of example, the prosthetic cardiac valve could be of the type described in U.S. Publication 2006/0178740 A1. As will be apparent to one skilled in the art, however, the instrument 1 could be used to deliver a variety of prosthetic cardiac valves and is not limited to any particular prosthetic valve structure.

As shown in FIG. 1, the instrument 1 includes a carrier portion 2 for enclosing and carrying the prosthetic device and a manipulation portion 3 that couples the carrier portion 2 to a control handle 4 where two actuator members (for instance two sliders 5, 6) are located. An optional third actuator is provided for that permits the carrier portion 2 to move forward, backward in relation to control handle 4. As will be appreciated, this feature permits for microadjustment of the carrier portion 2 and the valve prosthesis V in relation to a desired location while the control handle 4 is in a fixed location. A further optional actuator on the control handle 4 provides rotational adjustment of carrier portion 2 in relation to manipulation portion 3 and/or control handle 4. This permits the optional placement of the valve prosthesis through at least 360 degrees of rotation.

The manipulation portion 3 may assume various configurations. FIG. 1a shows a configuration where the portion 3 is comprised of a substantially rigid bar with a length (e.g., 10 cm) that will permit positioning of the carrier portion 3, and the prosthetic cardiac valve carried thereby, at an aortic valve site. As will be noted, instrument 1 is sized and dimensioned to permit easy surgical manipulation of the entire instruction as well as the actuators on the instrument without contacting parts of the subject in a way to interfere with the user's position of the valve prosthesis V.

This configuration is adapted for use, for example, in the sutureless and the transapical implantation methods. FIG. 1b, conversely, shows a second configuration, where the portion 3 is essentially comprised of an elongated, flexible catheter-like member that allows positioning of the carrier portion 3, and the prosthetic cardiac valve carried thereby, at an aortic valve site via transvascular catheterization (e.g., initiating at the femoral artery). This second configuration is also amenable for use in the sutureless or transapical implantation techniques. In one embodiment, the flexible, catheter-like member is braided or otherwise adapted to facilitate transmission of torque from the handle 4 to the carrier portion 2, such that the operator may effect radial positioning of the carrier portion 2 during the implantation procedure. Other features as described for the embodiment in FIG. 1a may also be added to the embodiment in FIG. 1b.

In one embodiment, the instrument 1 is adapted for use with a separate delivery tool. The instrument 1, for example, may be sized and shaped for delivery through a lumen of a tube or trocar during a "sutureless" or transapical delivery technique. Likewise, the instrument 1 may be adapted for delivery through a working lumen of a delivery or guide catheter. In this embodiment, for example, the operator may first deliver a guide catheter through the patient's vasculature to the implant site and then advance the instrument 1 through the lumen. According to another embodiment, the instrument 1 includes an axial lumen extending from a proximal end to a distal end. The lumen is sized to allow introduction and advancement of the instrument 1 over a previously-implanted guide wire. In other embodiments, other techniques known in the art are used to reach the implantation site from a location outside the patient's body.

Figure 2:
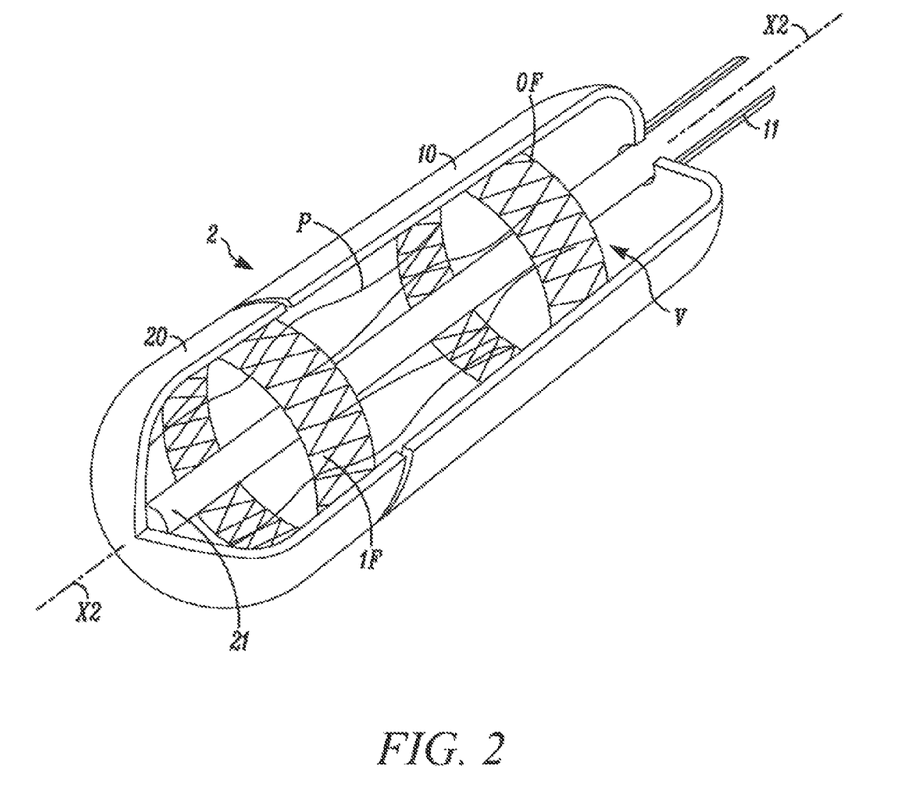
FIG. 2 is a partial cutaway, perspective view of a distal portion of the instrument of FIG. 1, according to one embodiment of the present invention.

As shown in FIG. 2, the carrier portion 2 includes two deployment elements 10, 20, each independently operable to allow the expansion of at least one corresponding, radially expandable portion of the implant device. In the case of the cardiac valve prosthesis, indicated as a whole as V, which is disclosed in U.S. Publication 2006/0178740 A1, two such radially expandable portions are provided situated respectively at the inflow end IF and the outflow end OF for the pulsated blood flow through the prosthesis. In alternative embodiments, however, the cardiac valve prosthesis may include more than two expandable members and, likewise, the carrier portion 2 may include more than two independent deployment elements. The valve prosthesis may be self-expanding (e.g., made from a superelastic material such as Nitinol) or may require expansion by another device (e.g., balloon expansion).

FIG. 2 illustrates an embodiment for use with a self-expanding cardiac valve prosthesis. As shown in FIG. 2, the cardiac valve prosthesis V is arranged within the carrier portion 2, such that an expandable portion IF and an expandable portion OF are each located within one of the deployment elements 10, 20. Each deployment element 10, 20 may be formed as a collar, cap or sheath. In yet a further embodiment, the elements 10, 20 are porous (or have apertures) such that blood flow is facilitated prior, during and after placement of prosthesis V. As will be appreciated, blood flows through the elements 10, 20 and over or through the prosthesis V during the placement procedure. Each deployment element 10, 20 is able to constrain the portions IF, OF in a radially contracted position, against the elastic strength of its constituent material. The portions IF, OF are able to radially expand, as a result of their characteristics of superelasticity, only when released from the deployment element 10, 20. Typically, the release of the portions IF, OF is obtained by causing an axial movement of the deployment elements 10, along the main axis X2 of the carrier portion 2. In one embodiment, the operator (e.g., physician) causes this axial movement by manipulating the sliders 5 and 6, which are coupled to the deployment elements 10, 20.

In yet an alternative embodiment, an optional micro-blood pump is operatively linked to the deployment elements 10 or 20 (or forms a part of the carrier portion 2, and serves to facilitate the movement of blood in a desired direction during the prosthesis placement procedure. The micro-blood pump can have a variable flow rate functionality to regulate blood flow as desired.

In an alternative embodiment (shown in FIGS. 7-9), expansion of the radially expandable portions IF, OF is caused by a positive expansion action exerted by the deployment elements 10, 20. In the embodiments shown in FIGS. 7-9, the deployment elements 10, 20 are comprised of expandable balloons onto which the portions IF, OF are coupled (e.g., "crimped") in a radially contracted position. In this embodiment, the operator causes radial expansion of the portions IF, OF by causing expansion of the balloons, using any of a variety of techniques.

Figure 3:
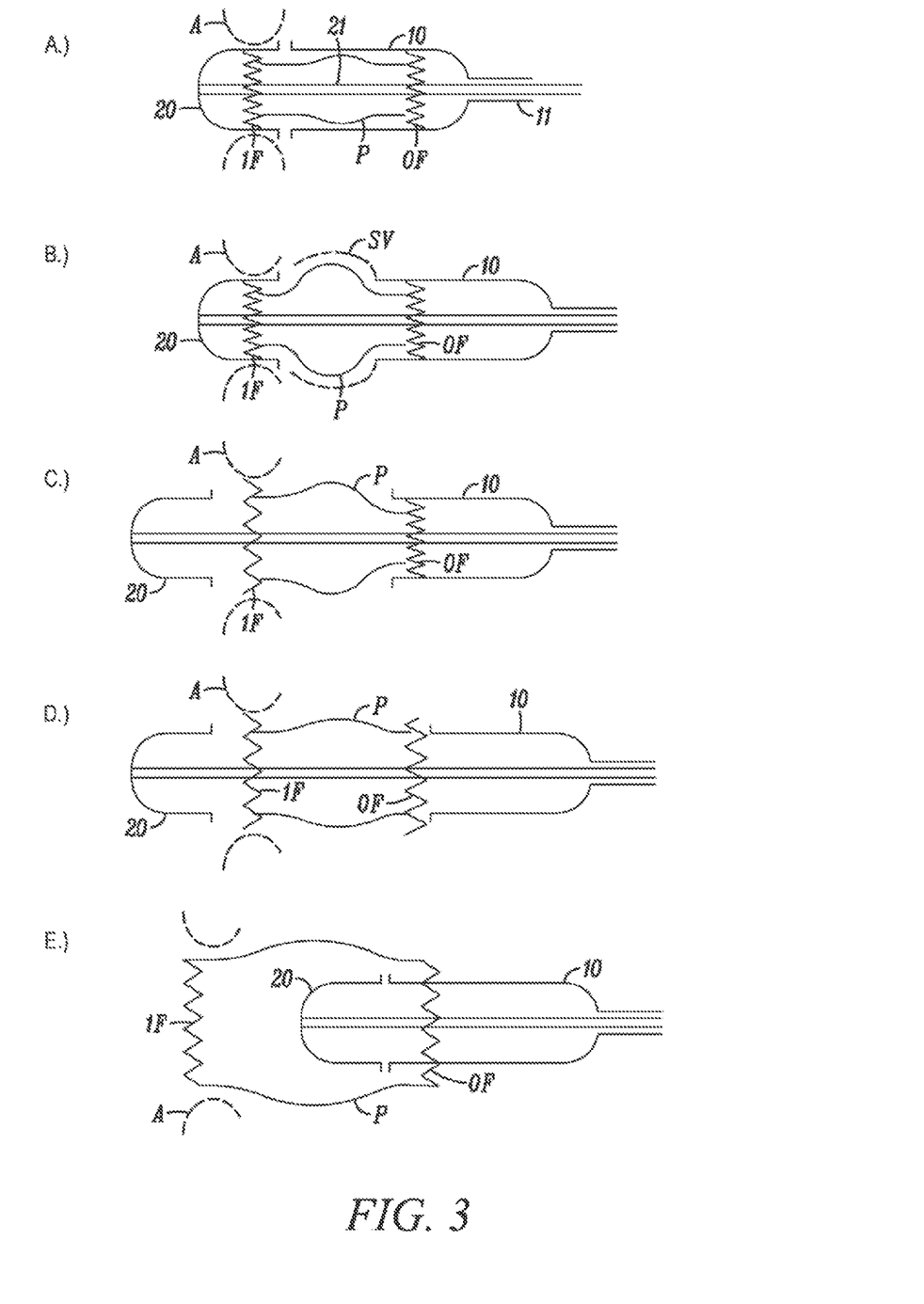
Figure 4:
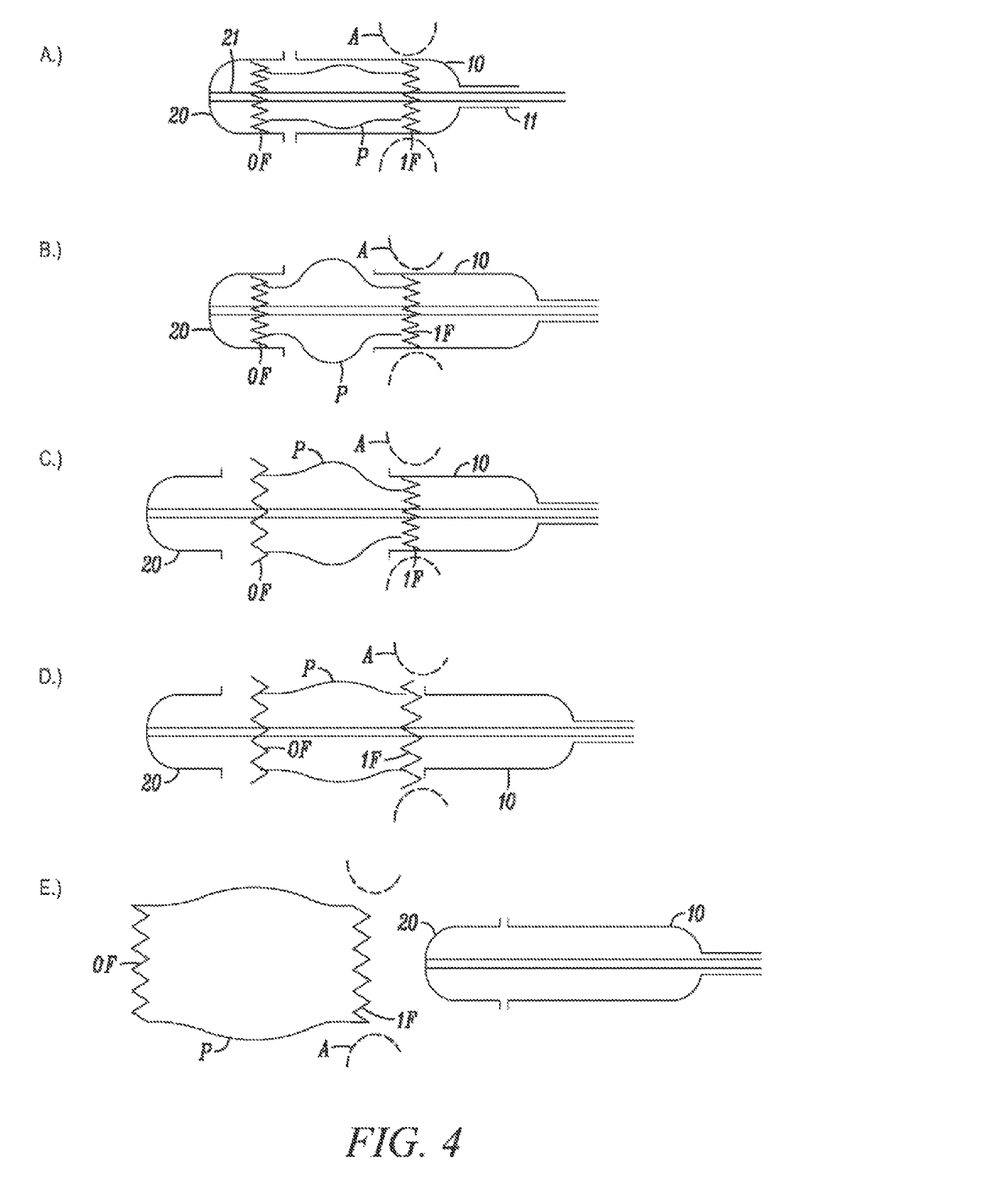
Figure 5:
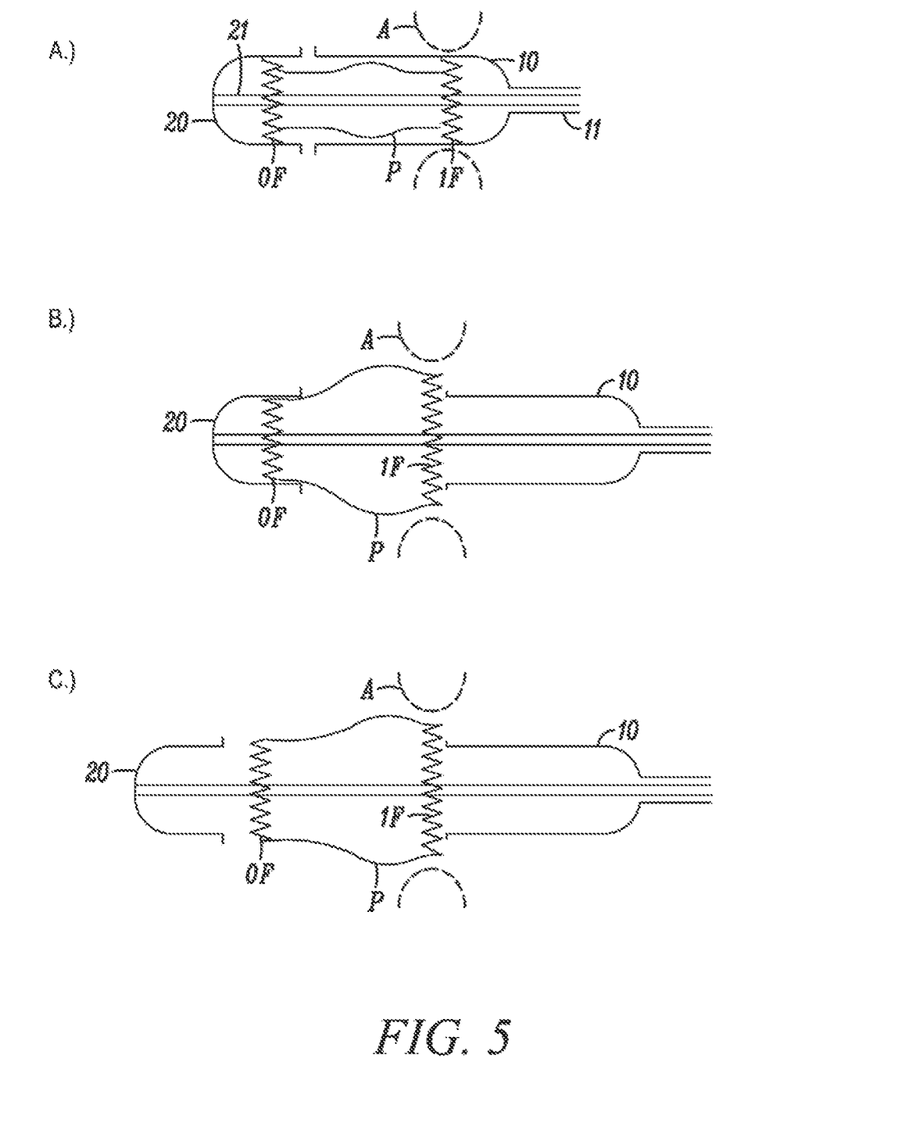

FIGS. 3-5 illustrate exemplary deployment techniques for the embodiment wherein the expandable portions IF, OF are made of a self-expandable material. In FIGS. 3-5, only the armature of the prosthetic cardiac valve prosthesis V is schematically shown (i.e., the valve leaflets are not shown). As shown, the armature includes the expandable entry (inflow) portion IF and the expandable exit (outflow) portion OF, which are connected axially by anchoring formations P. In one embodiment, as described in U.S. Publication 2006/0178740, the formations P are spaced at 120° intervals about the armature circumference and are configured to radially protrude from the prosthesis V so as to penetrate into the sinuses of Valsalva.

In the case of a cardiac valve prosthesis to be deployed at an aortic position, the inflow end IF of the prosthesis V is located in correspondence with the aortic annulus, thereby facing the left ventricle. The profile of the aortic annulus is shown schematically by the dashed lines A in FIGS. 3-5. Conversely, the outflow end OF is located in the ascending line of the aorta, in a position immediately distal to the sinuses of Valsalva, wherein the formations P extend. The elements 10, 20 are in a further embodiment sized and dimensioned to accommodate anchoring elements of prosthetic valve V. This dimensioning can take the form in one embodiment of appropriate tailored protuberances that permit the anchoring elements to rest in an appropriately contracted position prior to positioning.

FIGS. 3-5 show a carrier portion 2 having two deployment elements 10, 20 each of which is capable of "encapsulating" (on one embodiment) or restraining a respective one of the inflow IF and outflow OF portions, to constrain the portions IF, OF from radially expanding. Both the elements 10, 20 can be arranged to slide longitudinally with respect to the principal axis X2 of the carrier portion 2. In yet another variant, the elements 10, 20 slide down and rotate around the principal axis X2 (e.g. in a cork screw fashion). The axial (and optional rotational) movement of the elements 10, 20 is obtained, according to exemplary embodiments, via the sliders 5, 6 provided on the handle 4 at the proximal end of the manipulation portion 3 of the instrument 1. For instance, the slider 5 may act on the deployment element 20 through a respective control wire or tendon 21, while the slider 6 may act on the deployment element 10 through a tubular control sheath 11 slidably arranged over the tendon 21, with both the sheath 11 and tendon 21 slidable along the axis X2.

In one exemplary embodiment, an internal surface of the elements 10, 20 comprise a low-friction or lubricious material, such as an ultra-high molecular weight material or PTFE (e.g., Teflon®). Such a coating will enable the elements 11, 21 to move or slide with respect to the portions IF, OF, such that the portions IF, OF are released upon axial movement of the elements 11, 21. In yet a further embodiment, other surfaces of the elements 10, 20 or any other parts of device 1 are coated or made from a low-friction material to provide for ease of insertion and manipulation within a subject.

In one embodiment, the sheath 11 is movable in a distal-to-proximal direction, so that the sheath and thus the element 10 move or slide "backwards" with respect to the carrier portion 2. In a complementary manner, the sliding movement of the tendon 21 will take place in a proximal-to-distal direction, so that the tendon and thus the element 20 move or slide "forward" with respect to the carrier portion 2. In another embodiment, movement of the elements 10, 20 is obtained by manipulating rigid actuation members from the handle 4.

In yet a further embodiment, While the device 1 is shown as being manually operable by a user, it is within the spirit of the invention, to have device 1 and the various positioning elements actuated by sensors (positional) and movement of the various elements of the device control by servo-motors, a microprocessor, and the like (e.g., computer controlled). It is appreciated that placement of the prosthesis V may be more precisely controlled through computer control and mechanical movement of the various elements of device.

Figure 6:
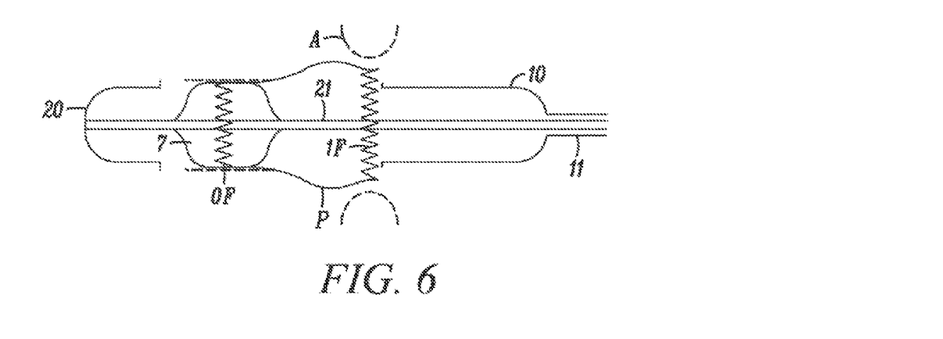
FIGS. 6-9 illustrate further possible features of the instrument illustrated herein, according to various embodiments of the present invention.

FIGS. 3-5 are deliberately simplified for clarity of representation and do not take into account, for instance, the fact that the portion 3 of the instrument may include other control tendons/sheaths and/or ducts for inflating the post-expansion balloons (see FIG. 6). Also, the element 20 could be actuated by means of a sheath rather than a tendon. Also, whatever their specific form of embodiment, the actuator members 11, 21 of the deployment elements 10, 20 may also have associated locking means (not shown, but of a known type) to prevent undesired actuation of the deployment elements 10, 20.

Notably, the deployment elements 10, 20 are actuatable entirely independently of each other. This gives the operator complete freedom in selecting which of the portions IF, OF to deploy first according to the specific implantation method or conditions. FIGS. 3a-3e, for example, illustrate use of the instrument 1 for a "retrograde" approach (e.g., in the case of sutureless or percutaneous implantation), to the valve annulus, wherein the cardiac valve prosthesis V approaches the valve annulus from the aortic arch.

In FIG. 3a (as in the following FIGS. 4a and 5a), the cardiac valve prosthesis V is shown mounted in or carried by the carrier portion 2 of the instrument 1, such that the deployment elements 10, 20 constrain the annular ends IF, OF of the prosthesis V in a radially contracted position.

FIG. 3b shows the element 10 retracted axially with respect to the axis X2 of the carrier portion 2 a sufficient distance to uncover and release the formations P, which are then able to expand (e.g., due to their superelastic construction) such that they protrude beyond the diameter of the elements 10, 20. As shown in FIG. 3b, the formations P are allowed to expand, while the remaining portions of the prosthesis V are maintained in a radially contracted configuration. In the configuration shown in FIG. 3b, the operator can take the necessary action for ensuring the appropriate positioning of the prosthesis V in correspondence with the sinuses of Valsalva SV. The profile of the sinuses of Valsalva are shown schematically in FIG. 3b by the dashed lines SV. Prosthesis V has elements sized and dimensioned to completely conform to the sinuses Valsalva in one variant of the invention.

Such appropriate positioning includes both axial positioning (i.e. avoiding deploying the prosthetic valve V too far "upstream" or too far "downstream" of the desired position with the ensuing negative effect that the inflow end IF is not correctly positioned with respect to the valve annulus A) and radial positioning. The sinuses of Valsalva are configured as a hollow, three-lobed structure. Accordingly, accurately positioning each formation P of the prosthesis V in a respective sinus of Valsalva will ensure the correct positioning or angular orientation of the prosthetic valve as a whole, which will ensure that the leaflets of the prosthetic valve are correctly oriented (i.e., extend at the angular positions of the annulus where the natural valve leaflets were located before removal).

In exemplary embodiments, the instrument 1 may further include various structures or features to assist the operator in obtaining the appropriate axial positioning with respect to the aortic annulus and radial positioning with respect to the sinuses of Valsalva. The instrument 1 (or the guide catheter or delivery tube), for example may include a lumen sufficient to allow the injection of contrast fluid to a location at the implantation site. For the embodiment shown in FIG. 3, for example, this lumen would have an opening located past the inflow end IF or the prosthesis V, such that any injected contrast fluid would then flow back toward the prosthesis V, thereby enabling the operator to obtain a visual image of the implantation site, including an image of the sinuses of Valsalva. Likewise, in other embodiments, the prosthesis V may include radiopaque markers disposed at appropriate locations to assist in this positioning.

In one exemplary embodiment (e.g., in the case of "sutureless" implantation), the carrier portion 2 and the prosthesis V may be arranged from the beginning in the configuration represented in FIG. 3*b*, namely with the formations P already protruding radially with respect to the profile of the prosthesis, while the annular end portions IF, OF are constrained in a radially contracted position by the elements 10, 20. In this case, the element 10 will have a sufficient length only to cover the axial extension of the annular end portion OF, as it need not radially constraint the formations P.

FIG. 3*c* shows the element 20 displaced distally with respect to the prosthesis V by the tendon 21. As shown, the element 20 was displaced a length sufficient to uncover the annular inflow portion IF, such that the portion IF is able to expand radially to assume the desired anchoring position at the valve annulus A. This release of the inflow portion IF takes place while the prosthetic valve V is still precisely retained and controlled by the instrument 1, such that it will not move or "jump" with respect to the valve annulus during the expansion of the portion IF.

It will also be appreciated that from the configuration shown in FIG. 3*c*, the operator may return to the configuration shown in FIG. 3*a*, so as to cause a radial contraction of the formations P and, even if in an incomplete manner, of the annular inflow portion IF. This will allow the operator to withdraw the prosthesis V from the implantation site if the operator believes that the implantation procedure has thus far not yielded a satisfactory result. In this variant, a re-contracting element is provided as part of device 1 that permits either the outflow OF and/or inflow IF portion to be re-constricted. By way of example a cutable thread could be used to re-crimp either portion.

Next, the prosthetic implantation process progresses by sliding the deployment element 10 so that it releases the outflow annular portion OF. The portion OF can then radially expand against the aortic wall, thus completing the second phase of the implantation operation of the prosthesis V.

Finally, as shown in FIG. 3*e*, the carrier portion 2 and the instrument 1 as a whole can be withdrawn with respect to the implantation site through the center of the prosthesis V. In one embodiment, the carrier portion 2 is withdrawn after the deployment elements 10, 20 have been brought back to their initial positions, that is after having caused the elements 10, 20 to slide, in a proximal-to-distal and in a distal-to-proximal direction, respectively. The sequence of operations represented in FIGS. 3*a*-3*e* may be accomplished with a pulsating heart and without interrupting the natural circulation of blood.

FIGS. 4*a*-4*e* show an implantation procedure of a prosthesis V, according to another embodiment of the present invention. This procedure is similar to the procedure shown in FIGS. 3*a*-3*e*, but FIGS. 4*a*-4*e* show an "antegrade" approach, typical of a transapical implantation procedure. In this case, the prosthesis V (mounted in the carrier portion 2) is advanced to the implantation site (e.g., aortic valve) through the left ventricle. While reference is again made herein to a prosthetic valve for the substitution of the aortic valve, it will be once more appreciated that the same criteria and principles will also apply to different valve types (e.g. mitral). Various techniques for accessing the aortic valve site through the left ventricle are known in the art. One exemplary technique for transapical delivery is disclosed in U.S. Publication 2005/0240200, which is incorporated by reference herein.

FIGS. 4*a*-4*e* are substantially identical to FIGS. 3*a*-3*e*, except that the position assumed by the prosthetic valve V is inverted. Accordingly, in the case of the intervention of "antegrade" type of FIGS. 4*a*-4*e*, the carrier portion 2 of the instrument 1 with the prosthesis V mounted therein is passed completely through the valve annulus A, so as to position the inflow portion IF in correspondence with the valve annulus A. As it is appreciated the device 1 is configured and sized and dimensioned so that it is capable of delivering the prosthesis V in both an antegrade and a retrograde intervention.

After withdrawing the deployment element 10, so as to release the formations P (FIG. 4*b*), the deployment element 20 is advanced distally, so as to release and allow the outflow annular end portion OF to radially expand against the aortic wall downstream of the sinuses of Valsalva (see FIG. 4*c*). At this point, the operator is still in a position to ensure that the prosthesis has the required correct angular position by making sure that the formations P each correctly engage a corresponding sinus. If the formations P do not properly align with the sinuses of Valsalva, the operator may use the instrument to apply a torque to the prosthesis V, thereby causing a rotation of the prosthesis V into the proper angular position. In one exemplary embodiment, the tendon 21 includes a stop (not shown) configured to prohibit axial motion of the inflow portion IF. This stop may help prevent axial movement of the inflow portion IF during distal motion of the of the deployment element 20, thereby ensuring that the outflow portion OF is released before the inflow portion IF.

Subsequently, by completely withdrawing in a proximal direction the deployment element 10, the operator releases the annular inflow portion IF that is thus deployed in correspondence with the aortic valve annulus thus completing the two-step implantation procedure of the prosthetic valve V (see FIG. 4*d*). Then, according to one embodiment, the procedure progresses by bringing the deployment elements 10, 20 back towards their initial position with the ensuing retraction of the instrument 1 from the inflow portion IF of the valve (FIG. 4*e*).

FIGS. 5*a*-5*c*, which correspond closely to the sequence of FIGS. 4*a*-4*c*, show that (also for a procedure of the "antegrade" type) it is possible to effect the two-step implantation sequence of FIGS. 4*a*-4*e* by deploying the end portions IF and OF of the prosthetic valve V in the reverse order. In the technique of FIGS. 5*a*-5*c*, once the desired "axial" position is reached (as represented in FIG. 5*a*, which is practically identical to FIG. 4*a*) with the expandable inflow end IF in correspondence of the aortic valve annulus A, the inflow portion IF is expanded first by operating the deployment element 10 to release the corresponding inflow portion IF.

The implantation procedure then proceeds, as schematically represented in FIG. 5*c*, with the second step of this two-step procedure, namely with the deployment element 20 advanced distally with respect to the prosthesis V so as to release the expandable outflow portion OF. The outflow portion OF is thus free to expand against the aortic wall in a region downstream of the sinuses of Valsalva into which the formations P protrude.

The teaching provided in FIGS. 5a-5c also apply in the case of a "retrograde" procedure, as shown in FIGS. 3a-3e. Because the deployment elements 10, 20 are adapted to be activated entirely independently of each other, the operator is free to choose the most suitable deployment sequence (inflow first and then outflow; outflow first and then inflow) as a function of the specific conditions of intervention. This sequence may be entirely independent of access to the implantation site being of the retrograde or antegrade type.

Figure 7:
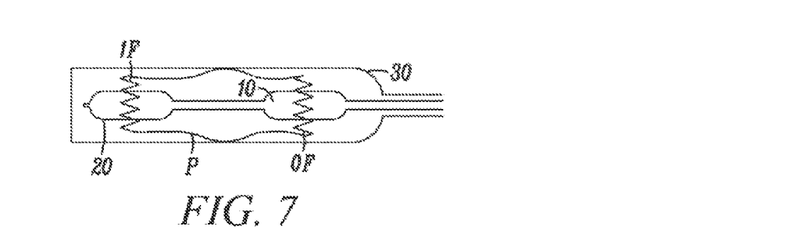

FIGS. 6 and 7 schematically illustrate embodiments in which the carrier portion 2 of the instrument 1 includes a balloon 7 at locations corresponding to at least one or to both annular ends of the cardiac valve prosthesis V. This balloon may be of any known type (e.g. of the type currently used in expanding stents or the like in a body lumen, which therefore does require a detailed description to be provided herein) and is intended for use in realizing a "post-expansion" of the corresponding end portion IF, OF of the prosthesis V, so as to radially urge it against the wall of the implantation lumen. For instance, as shown in FIG. 6, the balloon 7 can be selectively expanded (by inflating it with well known means and criteria) in such a way as to produce a radial expansion of the expandable portion associated therewith (here the end portion OF).

This technique may be useful to avoid movement or "jumping" of the prosthesis V during implantation. For instance, if the operator fears that deployment of the inflow end portion IF in correspondence of the aortic annulus A may give rise to an undesired longitudinal displacement of the valve prosthesis V as a whole, while the inflow portion IF is being released by the element 10 and expands to engage the aortic annulus A, a post-expansion balloon 7 associated with the outflow end OF can be inflated. In this way, as long as the post-expansion balloon 7 is kept dilated, the outflow end OF is urged and thus safely anchored to the lumen wall and any undesired displacement of the prosthetic valve V in an axial direction is prevented. Once the inflow portion IF is safely positioned at the aortic annulus A, the balloon 7 can be deflated and the instrument 1 withdrawn.

Figure 8:
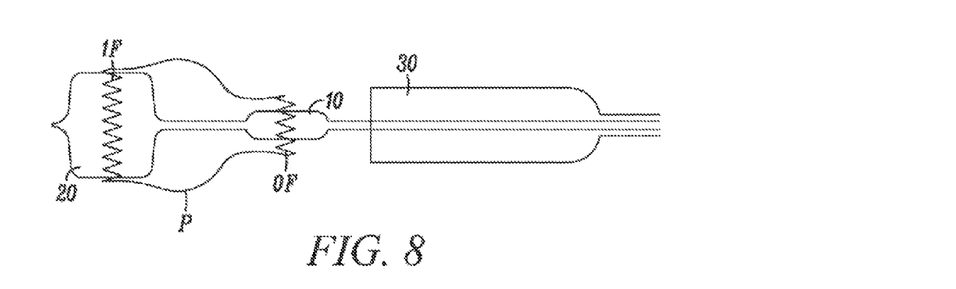
Figure 9:
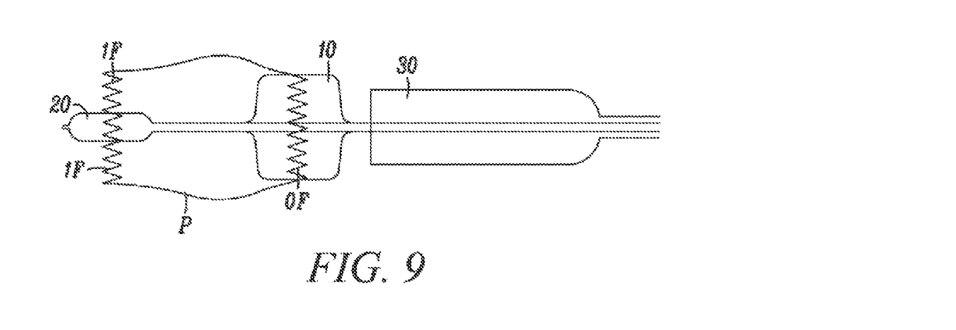

FIGS. 7, 8 and 9 schematically illustrate, without the intent of making any specific distinctions between "antegrade" and "retrograde" approaches and any specific choice as to which end portion, inflow IF or outflow OF, is to be deployed first, that the same two-step mechanism for independently deploying the two end portions IF, OF illustrated in FIGS. 3, 4 and 5 can be implemented in the case of prostheses V including end portions IF, OF whose radial expansion is obtained via a positive outward expansion action exerted by means of deployment elements 10, 20 altogether constituted by expandable balloons. These may be balloons of any known type and substantially correspond, from a structural point of view, to the post-expansion balloons (see for instance the balloon 7 of FIG. 6).

Other embodiments of the present invention include "hybrid" solutions, where a cardiac valve prosthesis V includes one or more self-expandable portions (having associated deployment elements 10, 20 of the type illustrated in FIGS. 2-5) as well as one or more portions radially expandable via an expandable deployment element (such as a balloon as illustrated in FIGS. 7-9).

In one variant and in the case where expansion due to a positive action of one or more balloons is preferred over the use of a self-expandable portion, the same balloon may be used both as an expansion balloon (FIGS. 7, 8 and 9), and as a post-expansion balloon (FIG. 6).

As schematically illustrated in FIGS. 7-9 (the same solution can be adopted also in the case of FIGS. 2-6, it is possible to provide a tubular sheath 30 that surrounds in the manner of a protective tunic the assembly comprised of the carrier portion 2 with the prosthetic valve V mounted therein. This with the purpose of facilitating, typically in a percutaneous implantation procedure, the advancement towards the implantation site through the tortuous paths of the vasculature of the patient without risks of undesired jamming or kinking. It will be appreciated that, for the same goal, the deployment elements 10, 20 normally exhibit a "streamlined" shape, exempt from protruding parts and/or sharp edges. This is particularly the case for the element 20 located at a distal position, which typically exhibits an ogive-like shape.

In yet another variant of the invention, the elements 10, 20 are formed of a material that permits them to collapse after deployment of the prosthesis V. It is appreciated that this permits the entire device to be more easily removed from the subject.

FIGS. 10a-10d, which substantially correspond to FIGS. 5a-5c, illustrate an embodiment associating with either or both of the annular end portions IF, OF of the prosthesis V and "anti-skid" locking member 22. This member is primarily intended to prevent any undesired sliding movement of the end portion (IF and/or OF) with respect to its deployment element lengthwise of the carrier portion 2. Such a locking member is preferably associated with (at least) the annular end portion to be deployed second in the two-step deployment process of the prosthetic valve V described herein.

Figure 10:
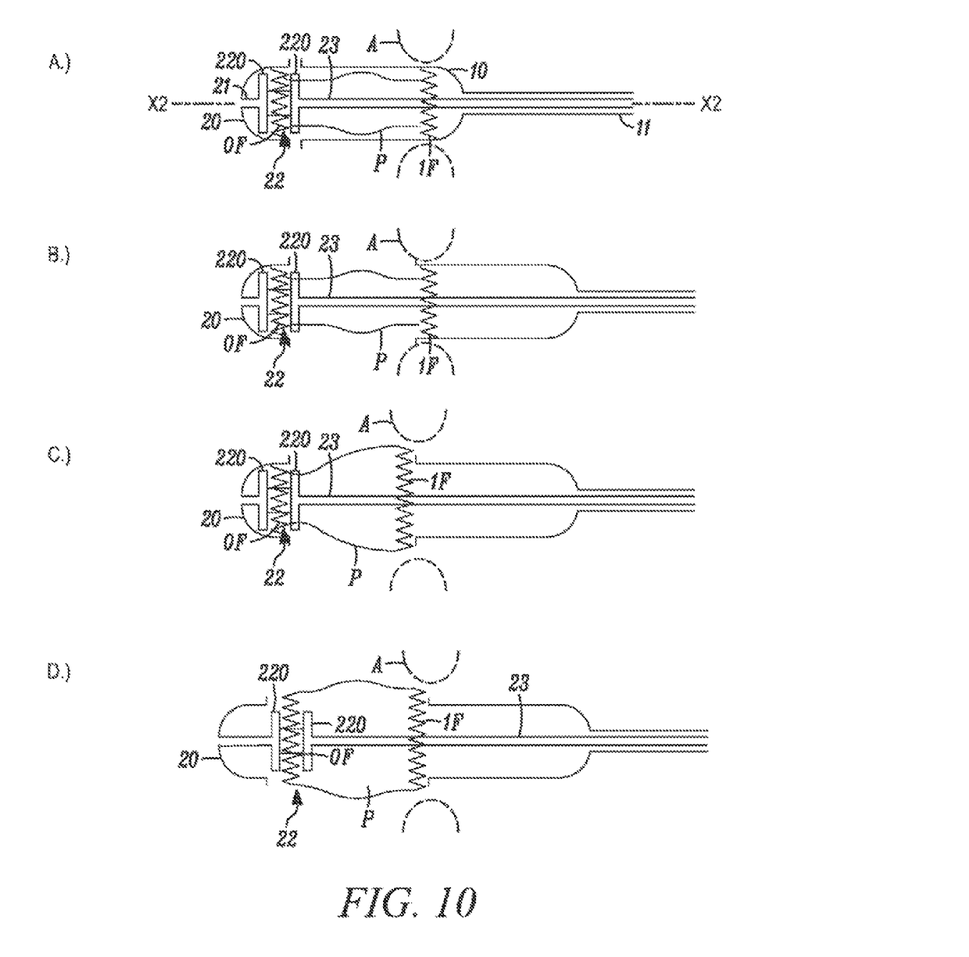

In this exemplary embodiment, the locking member 22 takes the form of a hub positioned at the distal end of a tubular member 23 having the wire 21 slidably arranged therein. The sheath 11 surrounds the tubular member 23 and is adapted to slide thereon so that the locking member 22 is capable of maintaining at a fixed axial position (e.g. via end flanges 220) the annular outflow portion OF with which the locking member is associated. The annular end portion in question is thus prevented from sliding axially of the deployment element 20, at least as long as the annular end portion OF is radially constrained by the deployment element 20.

The arrangement described makes it possible to adjust the position of the annular end portion locked by the locking member (and the position of the valve prosthesis V as a whole) both axially and angularly to the implantation site. This applies more or less until the annular portion expands to the point where further displacement is prevented by engagement of the annular portion with the valve annulus or the aortic wall. Additionally, the presence of the locking member (s) 22 facilitates possible recovery of the prosthetic valve V in case the implantation procedure is to be aborted.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A cardiac valve implantation system for implanting a mitral valve prosthesis at an implantation site associated with a mitral valve annulus, the system comprising:
   an expandable mitral valve prosthesis including an annular inflow portion, an annular outflow portion, and a plurality of valve leaflets;
   a deployment instrument including:
      a control handle;
      a carrier portion for enclosing and carrying the mitral valve prosthesis, the carrier portion including:

a first independently operable deployment element operable to deploy the annular inflow portion at an atrial side of a mitral valve annulus, such that the annular inflow portion is located within the first deployment element when radially constrained;

a second independently operable deployment element operable to deploy the annular outflow portion at a ventricular side of a mitral valve annulus, such that the annular outflow portion is located within the second deployment element when radially constrained; and a sheath that is attached to and extends proximal to the first deployment element;

a tubular member extending from the control handle and through the carrier portion, wherein the sheath of the carrier portion is configured to slide on the tubular member;

a wire extending from the control handle to the second deployment element and slidably arranged within the tubular member;

a locking member comprising a hub positioned on a distal end of the tubular member, the hub comprising a first end flange and a second end flange that are configured to maintain the annular outflow portion at a fixed axial position along the tubular member in order to prevent any undesired sliding movement of the annular outflow portion with respect to the second deployment element lengthwise of the carrier portion as long as the annular outflow portion is radially constrained by the second deployment element, wherein the first end flange is arranged proximal to the annular outflow portion and the second end flange is arranged distal to the annular outflow portion when the annular outflow portion is maintained at a fixed axial position by the locking member, and wherein the tubular member is connected to the first and second end flanges; and a delivery device adapted to provide a pathway from outside the patient's body for delivery of the deployment instrument to the implantation site.

2. The system of claim 1, wherein the mitral valve prosthesis comprises a plurality of expandable members.

3. The system of claim 1, wherein the mitral valve prosthesis is self-expandable.

4. The system of claim 1, wherein the deployment elements each comprise a sheath.

5. The system of claim 1, wherein the deployment elements each comprise a collar.

6. The system of claim 1, wherein the deployment elements each comprise a cap.

7. The system of claim 1, wherein the deployment elements are porous.

8. The system of claim 1, wherein the deployment elements include apertures.

9. The system of claim 1, wherein the annular outflow portion and annular inflow portion are releasable by axial movement of the deployment elements along the deployment instrument.

10. A system for implanting a mitral valve prosthesis in a patient's heart, comprising, in combination, an expandable, tissue, stented mitral valve prosthesis including an annular inflow portion and an annular outflow portion, and a valve delivery device for delivering the stented mitral valve prosthesis to a mitral valve annulus in the patient's heart, the delivery device comprising:

a deployment module for expanding the stented mitral valve prosthesis, the deployment module comprising:
a control handle;
a carrier portion for enclosing and carrying the mitral valve prosthesis, the carrier portion including:
a first deployment element operable to deploy the annular inflow portion at an atrial side of a mitral valve annulus and configured to enclose the annular inflow portion when radially constrained, wherein the first deployment element is actuatable in an axial direction to allow the annular inflow portion to expand;

a second deployment element operable to deploy the annular outflow portion at a ventricular side of a mitral valve annulus and configured to enclose the annular outflow portion when radially constrained, wherein the second deployment element is actuatable in an axial direction to allow the annular outflow portion to expand; and a sheath that is attached to and extends proximal to the first deployment element;

a tubular member extending through the carrier portion, wherein the sheath of the carrier portion is configured to slide on the tubular member;

a wire extending from the control handle to the second deployment element and slidably arranged within the tubular member;

a locking member comprising a hub positioned on a distal end of the tubular member, the hub comprising a first end flange and a second end flange that are configured to maintain the annular outflow portion of the prosthesis at a fixed axial position when radially constrained;

wherein each of the first and second deployment elements are independently operable, and wherein the locking member is configured to prevent any undesired sliding movement of the annular outflow portion with respect to the second deployment element lengthwise of the carrier portion as long as the annular outflow portion is radially constrained by the second deployment element wherein the first end flange is arranged proximal to the annular outflow portion and the second end flange is arranged distal to the annular outflow portion when the annular outflow portion is maintained at a fixed axial position by the locking member, and wherein the tubular member is connected to the first and second end flanges.

11. The system of claim 10, wherein the mitral valve prosthesis comprises a plurality of expandable members.

12. The system of claim 10, wherein the mitral valve prosthesis is self-expandable.

13. The system of claim 10, wherein the deployment elements each comprise a sheath.

14. The system of claim 10, wherein the deployment elements each comprise a collar.

15. The system of claim 10, wherein the deployment elements each comprise a cap.

16. The system of claim 10, wherein the deployment elements are porous.

17. The system of claim 10, wherein the deployment elements include apertures.

18. The system of claim 10, wherein the annular outflow portion and annular inflow portion are releasable by axial movement of the deployment elements along the deployment module.

* * * * *